United States Patent [19]

Grass

[11] Patent Number: 5,599,688
[45] Date of Patent: Feb. 4, 1997

[54] DEVICE AND METHOD FOR CIRCULATING FLUID OVER A MEMBRANE

[75] Inventor: George M. Grass, Tahoe City, Calif.

[73] Assignee: Precision Instrument Design, Tahoe City, Calif.

[21] Appl. No.: 506,049

[22] Filed: Jul. 24, 1995

Related U.S. Application Data

[63] Continuation of Ser. No. 138,653, Oct. 18, 1993, abandoned.

[51] Int. Cl.$^6$ .............................. C12Q 1/02; C12M 3/06; C12M 1/12
[52] U.S. Cl. ..................... 435/29; 435/287.1; 435/287.9; 435/297.2; 73/38; 73/64.47; 324/450; 324/71.1; 422/101
[58] Field of Search .................................. 435/29, 34, 39, 435/40, 240.241, 809, 817, 173.1, 173.4–173.6, 287.1, 287.9, 288.2, 288.1, 288.4, 288.5, 289.1, 288.3, 292.2, 304.2, 305.1, 305.2, 304.1; 422/99, 101, 102, 104, 48; 73/38, 64.47; 210/321.75, 321.84; 204/400, 403, 415, 153.1, 153.12; 324/439, 444, 446, 450, 692, 71.1

[56] References Cited

U.S. PATENT DOCUMENTS 3,186,917 6/1965 Gerhardt et al. ............................. 195/1
3,342,729 9/1967 Strand ....................................... 422/48

(List continued on next page.)

FOREIGN PATENT DOCUMENTS 0033362 8/1980 Japan ................................. 210/321.75

OTHER PUBLICATIONS

Grass, George M. et al. "In Vitro Measurement of Gastrointestinal Tissue Permeability Using a New Diffusion Cell," *Pharmaceutical Research*, vol. 5, No. 6, 1988 pp. 372–376.

"Membrane separations in biotechnology," Library of Congress Cataloging–in–Publication Data, Copyright © 1986, pp. 284–300.

Schoenwald, Ronald D. et al. "Corneal Penetration Behavior of β–Blocking Agents I: Physicochemical Factors," *Journal of Pharmaceutical Sciences*, vol. 72, No. 11, Nov. 1983 pp. 1266–1281.

Ussing, Hans H. et al. "Active Transport of Sodium as the Source of Electric Current in the Short–circuited Isolated Frog Skin," *Acta phys. Scandinav.* vol. 23, Dec. 23, 1950, pp. 110–127.

Product Brochure "Diffusion chamber system for cells cultured on Costar Snapwell™ microporous membranes," Precision Instruments Design. (Jan. 25, 1994).

*Primary Examiner*—William Beisner
*Attorney, Agent, or Firm*—Townsend and Townsend and Crew

[57] ABSTRACT

The invention provides a compact device and simple method for circulating fluid over the surface of a membrane. The device comprises a housing that in combination with the surface of the membrane defines an enclosed volume through which the fluid is circulated. Some embodiments will include a membrane holding layer, a fluid dispersing layer, or both. The membrane holding layer has an opening through it to expose a predetermined surface area of the membrane to the fluid. The dispersing layer has a set of openings, typically slits, through the dispersing layer to disperse fluid over the surface of the membrane. Some embodiments may include electrodes for sensing or applying electrical potential to the membrane. A particularly preferred embodiment comprises a double sided device including a first housing, dispersing layer and membrane holding layer on one side of a membrane and a second housing dispersing layer and membrane holding layer on the other side of the membrane. A separate fluid may be circulated through each housing over the two sides of the membrane. In some embodiments the membrane will be provided with at least one ridge that defines at least two parallel channels in which different types of cells may be held.

24 Claims, 7 Drawing Sheets

U.S. PATENT DOCUMENTS

| | | | |
|---|---|---|---|
| 3,386,912 | 6/1968 | Lazare | 210/22 |
| 3,508,656 | 4/1970 | Serfass et al. | 210/90 |
| 3,520,803 | 7/1970 | Iaconelli | 210/23 |
| 3,684,097 | 8/1972 | Mathewson et al. | 422/48 |
| 3,963,613 | 6/1976 | Chibata et al. | 210/195 R |
| 4,087,327 | 5/1978 | Feder et al. | 195/1.7 |
| 4,212,742 | 7/1980 | Solomon et al. | 210/321.84 |
| 4,395,492 | 7/1983 | Rees | 435/283 |
| 4,446,229 | 5/1984 | Indech | 435/1 |
| 4,508,819 | 4/1985 | Rose | 435/1 |
| 4,537,860 | 8/1985 | Tolbert et al. | 435/240 |
| 4,661,458 | 4/1987 | Berry et al. | 435/284 |
| 4,666,853 | 5/1987 | Meserol et al. | 435/290 |
| 4,667,504 | 5/1987 | Hobson | 73/38 |
| 4,686,190 | 8/1987 | Cramer et al. | 435/291 |
| 4,734,372 | 3/1988 | Rotman | 422/48 |
| 4,846,970 | 7/1989 | Bertelsen et al. | 73/38 |
| 4,852,389 | 8/1989 | Mayer et al. | 73/38 |
| 4,938,931 | 7/1990 | Cussler | 422/211 |
| 5,183,760 | 2/1993 | Sweetana et al. | 435/285 |
| 5,190,878 | 3/1993 | Wilhelm | 435/285 |

DEVICE AND METHOD FOR CIRCULATING FLUID OVER A MEMBRANE

This is a Continuation of application Ser. No. 08/138,653, filed Oct. 18, 1993, now abandoned.

BACKGROUND OF THE INVENTION

1. Field of the Invention

The invention provides apparatus and methods for holding and circulating fluids over a membrane. The invention may find use in laboratory studies of the transport and absorption of substances by membranes including biological tissues, cell cultures, and synthetic materials. The invention will also be useful for performing toxicology studies in which substances of interest are circulated over cultured cells to study the effects of those substances on the cells. The invention may also find use in culturing cells in vitro.

2. Description of the Background Art

Hobson, U.S. Pat. No. 4,667,504, issued May 26, 1987, discloses an apparatus for determining in vitro the penetration rate of chemicals across a biological membrane. The apparatus comprises two housings, one holding a reservoir of test chemical, and the other providing a chamber for flowing receptor solution across a membrane held in a membrane holding compartment. The membrane holding compartment comprises a cylindrical depression surrounding an open end of the receptor solution chamber. The receptor solution chamber is tilted slightly with its higher end open to the membrane holding compartment. The tilt prevents bubbles in the receptor solution from becoming stalled or trapped inside the chamber and interfering with the reliability and reproducibility of tests. An inlet bore from the upper surface of the receptor housing leads to a closed end of the chamber near the membrane holding compartment to the upper surface of the receptor housing. The inlet bore is sized smaller than the outlet bore. The depth of the depression forming the membrane holding compartment varies, tapering from a lesser depth at its intersection with the chamber to a greater depth at the outer circumference of the depression. The thus formed truncated cone ensures that a sample biological membrane is stretched taut over the chamber opening by the force fastening the reservoir housing to the receptor solution housing.

The publication of Ussing and Zerahn (Acta Physiol. Scand. 23:110–127 (1951)) describes an apparatus for the determination of sodium flux and short circuit current in frog skin. The device has an area for placement of the skin between two opposing half cells, pressed against the skin by two lucite screws held by steel uprights. The tips of the lucite screws are conical and fit into conical depressions in the center of the ebonite dishes. Buffer solutions are circulated and aerated by air entering through side tubes. Bridges, held in position by pieces of rubber tubing, fit tightly into short celluloid side tubes sealed into the two chambers and these connect to a reservoir system. The device is also fitted with a series of electrodes.

Schoenwald and Huang (J. Pharm. Sci. 72:11 (1983)) discloses a device for mounting of corneas to determine transport of material across corneal tissue. The system is composed of two acrylic plastic blocks. Each block acts as an opposing half cell with an area for the corneal tissue between. The cornea is mounted using a system of three rings, and the ring system with the cornea is positioned in the opening of the blocks and forms a water-tight seal when sufficient lateral pressure is applied to the blocks in a manner similar to that described above by Ussing and Zerahn. Fluid reservoirs on each side of the tissue are mixed with a gas lift mechanism, also similar to Ussing and Zerahn above. Stirring motors mounted on the blocks connect by shafts with blades on the terminus through the block to the reservoir at the tissue face. These blades promote mixing at the tissue surface. The reservoirs are heated by circulation of temperature controlled fluid through channels in the block. the fluid reservoirs and fluid circulation channels for temperature control are within the same contiguous block.

Hidalgo et al. (Gastroenterology 96:736–49 (1989)) disclose a method for the measurement of transport of material across a monolayer formed by cultured cells. Cells are grown in an appropriate medium in a plastic cylinder which is capped at one end with a filter membrane. When the cells reach a confluent monolayer, the cells and the cylinder with attached filter are placed in another larger diameter cylinder with fluid which acts as the receiver solution. Materials placed in the smaller cylinder with the cells are transported across the cells and the filter membrane to the reservoir solution of the larger cylinder.

Grass and Sweetana (Pharm. Res. 5:6 (1988)) disclose a diffusion cell chamber for the measurement of tissue permeability. The apparatus is comprised of at least one chamber with a first and a second volume element, each of which contains a reservoir for fluids and a means to circulate fluids. Also included is a means to retain a membrane separating the first and second volume elements whereby the fluid contained in the reservoir in the first volume element housing could communicate with the fluid contained in the reservoir in the second volume element in the absence of the membrane. Also included are a membrane separating the first and second volume elements, a means to circulate fluid contained in each of the first and second volume elements, and a means to attach the first and second volume elements on a contiguous surface of each of the first and second volume elements in an adjacent facing relationship, wherein the first and second volume element housings are separated from each other at their contiguous surfaces by the membrane. Substantially the same apparatus is disclosed in Sweetana et al, U.S. Pat. No. 5,183,760, issued May 26, 1987.

The disclosure of each of the above publications is incorporated herein by reference.

SUMMARY OF THE INVENTION

The invention provides a compact device and simple method for circulating fluid over the surface of a membrane. The device comprises a housing that in combination with the surface of the membrane defines an enclosed volume through which the fluid is circulated. Some embodiments will include a membrane holding layer, a fluid dispersing layer, or both. The membrane holding layer has an opening through it to expose a predetermined surface area of the membrane to the fluid. The dispersing layer has a set of openings, typically slits, through the dispersing layer to disperse fluid over the surface of the membrane. Some embodiments may include electrodes for sensing or applying electrical potential to the membrane.

A particularly preferred embodiment comprises a double sided device including a first housing, dispersing layer and membrane holding layer on one side of a membrane and a second housing, dispersing layer and membrane holding layer on the other side of the membrane. Each housing includes means for circulating a fluid through it over the membrane.

In some embodiments the membrane will be provided with at least one ridge that defines at least two parallel channels in which different types of cells may be held.

A device according to the invention may find use in performing studies of the transport characteristics of substances across membranes, for studying the effect of fluid-borne substances on cells, for culturing cells in vitro, and the like.

DESCRIPTION OF SPECIFIC EMBODIMENTS

The invention provides a device and method for holding and circulating fluid over the surface of a thin film membrane. The membrane may be, for example, a thin sheet of biological tissue, a synthetic material, or a layer of cultured cells grown on a suitable support.

Figure 1:
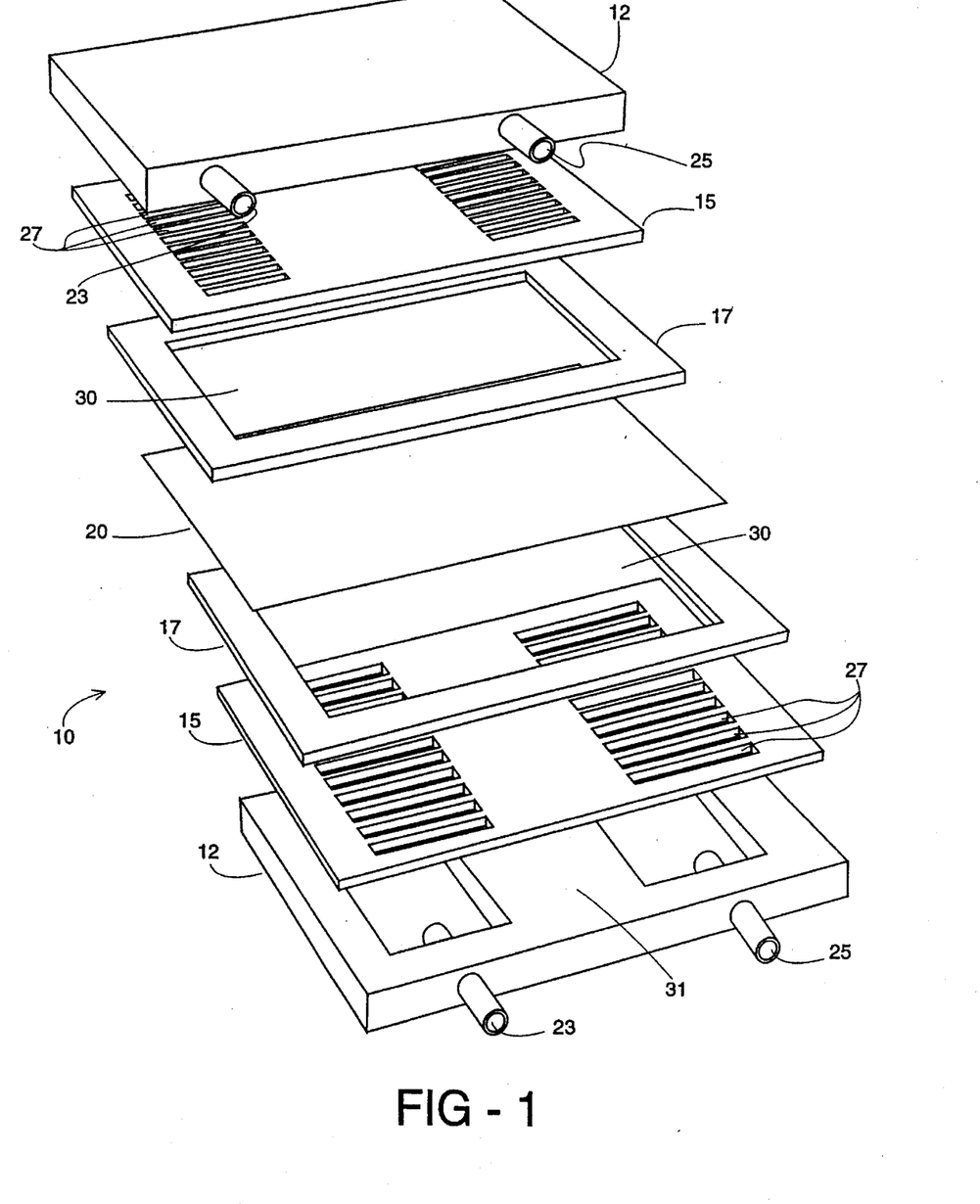
FIG. 1 depicts the constituent parts of a device according to the invention.
Figure 2:
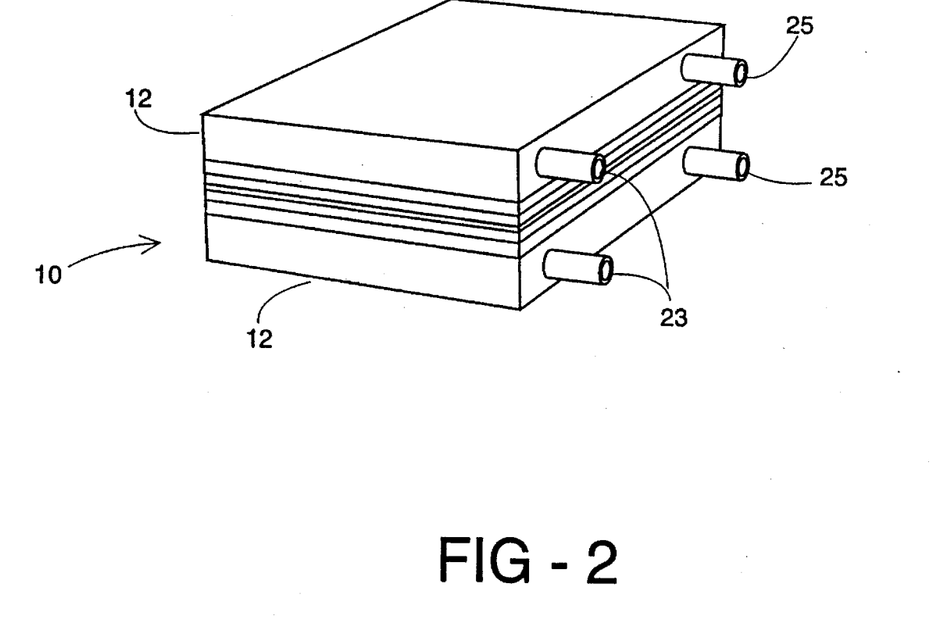
FIG. 2 shows the device of FIG. 1 assembled.

FIG. 1 shows the constituent parts of a membrane holding device 10 according to the invention. FIG. 2 shows device 10 assembled. The preferred embodiment depicted in FIG. 1 comprises first and second housings 12, first and second dispersing layers 15, and first and second membrane holding layers 17. When the device is assembled, a thin membrane 20 is held between first and second membrane holding layers 17.

Each housing is provided with an inlet 23 and an outlet 25. The inlet and outlet provide means for circulating fluid through the enclosed volume defined between the housing and the membrane. As fluid is circulated through the housing, the fluid will be dispersed through slits 27 or other openings in dispersing layer 15. The fluid will then travel through an opening 30 in membrane holding layer 17 and across the exposed surface of membrane 20. The opening in the membrane holding layer ensures that only a predetermined surface area of the membrane is exposed to the fluid.

Because the fluid flows across the surface of the membrane, the invention may be particularly useful in applications involving endothelial cells such as those that line the interior of the capillaries. In their natural state, these cells have fluid, blood, flowing across their surface. This gives rise to a shear force on the surface of the cells. The invention simulates this natural state better than do stagnant reservoir devices. Furthermore, the membrane may be made flexible, with some degree of slack in it. If the fluid is pulsed through the housing, the membrane will flex rhythmically along with the pulsation of the fluid. Cardiac cells in particular may benefit from this.

Figure 3A:
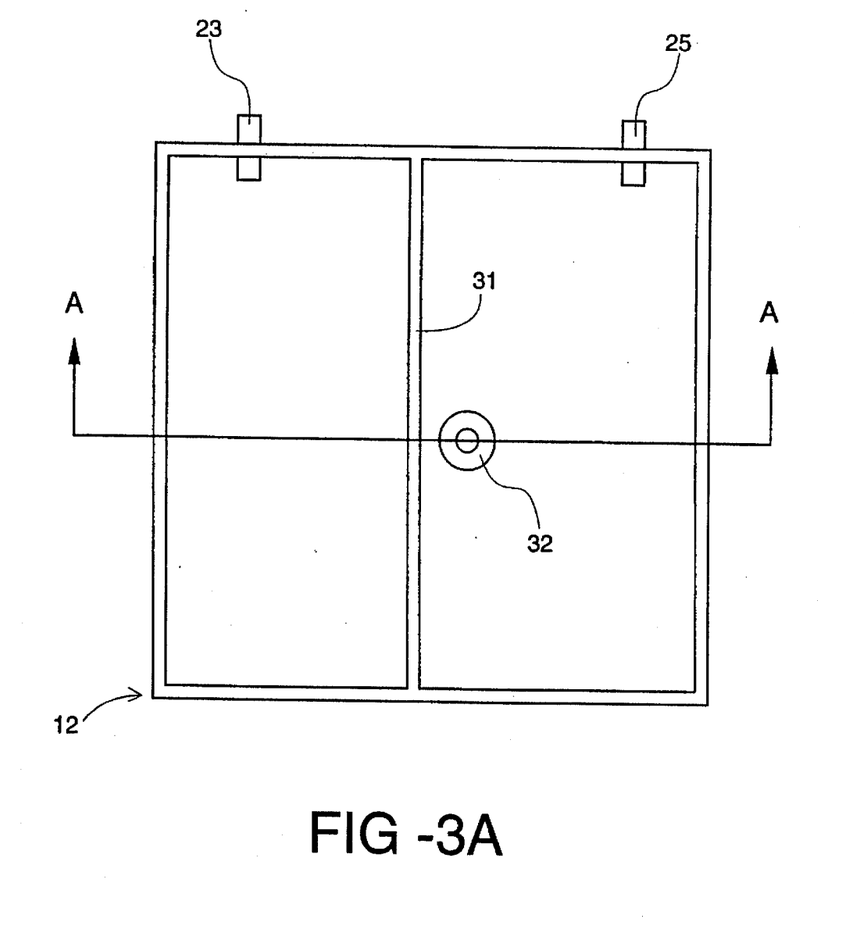
FIG. 3A shows the interior of the housing of the device of FIG. 1.
Figure 3B:
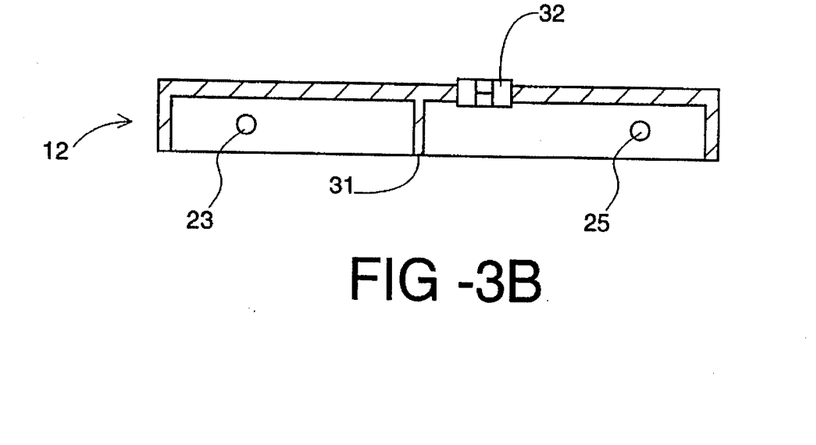
FIG. 3B is a sectional view through section line A—A of FIG. 3A

FIG. 3A provides a view of the interior of housing 12. FIG. 3B is a sectional view of the housing through section line A—A of FIG. 3A. As can be seen in FIGS. 3A and 3B, housing 12 includes a divider 31 across its center between inlet 23 and outlet 25. Divider 31 ensures that fluid entering the enclosed volume through inlet 23 is forced through slits 27 and over the surface of the membrane. After flowing across the surface of the membrane, the fluid flows back through the slits on the other side of the dispersing layer and back out of the housing through outlet 25. If the divider were not present, the bulk of the fluid might simply travel through the housing without flowing through the slits or flowing over the surface of the membrane.

Divider 31 may be relatively thin as depicted in FIGS. 3A and 3B, or it may be somewhat wider as depicted in FIG. 1. A relatively wide divider may be advantageous in some cases because it reduces the fluid volume within the housings and because it provides more support to the membrane.

FIGS. 3A and 3B also depict an injection port 32 through the housing. In some cases, e.g., when cells are to be grown on the membrane, it will be desirable to inject cells through the housing and onto the surface of the membrane. A hypodermic needle may be inserted into the housing through port 32 to accomplish this. The injection port may include a self-sealing central portion to allow entry of the hypodermic needle while sealing itself after the needle is withdrawn. This may be accomplished by providing the injection port with a pliable rubber or silicone central portion. When the needle is withdrawn, the opening through the central portion closes, resealing the housing.

Figure 4A:
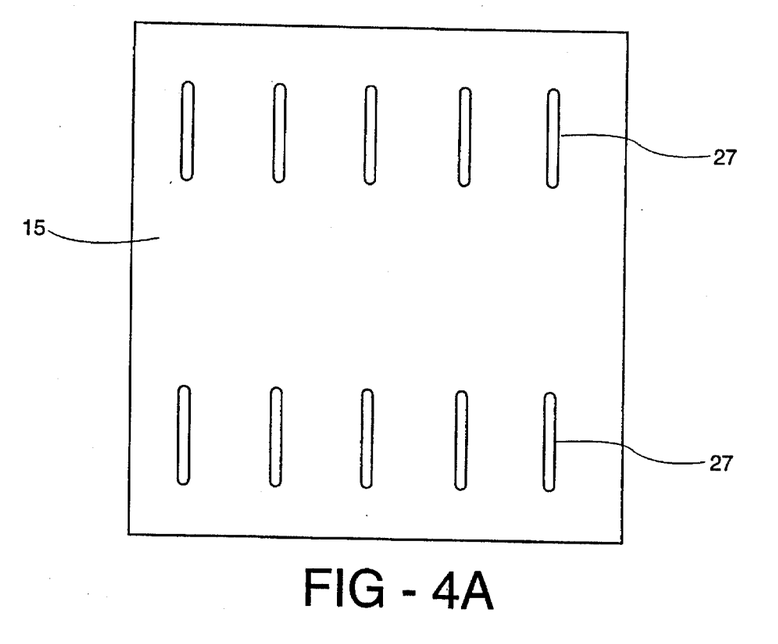
FIGS. 4A and 4B depict dispersing and membrane holding layers for use in the device of FIG. 1.
Figure 4B:
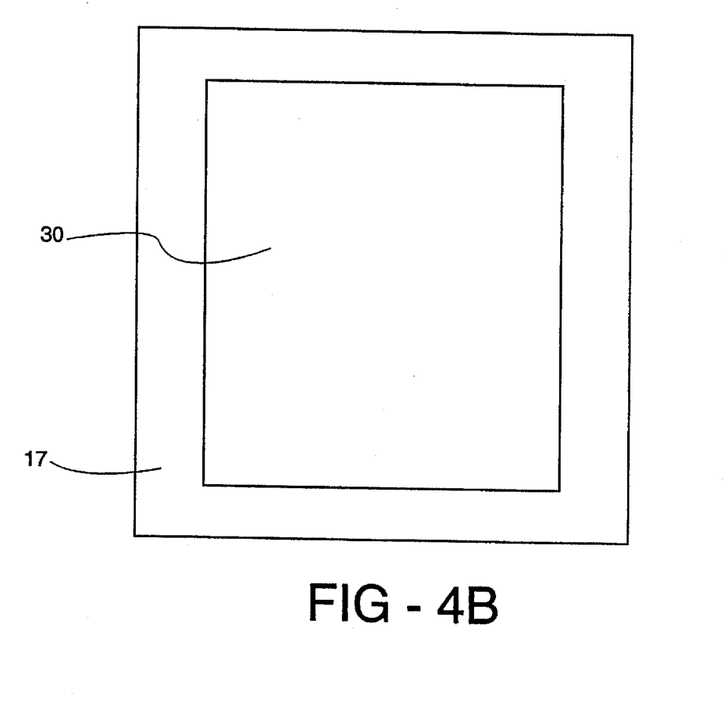

Dispersing layer 15 and membrane holding layer 17 are depicted in FIGS. 4A and 4B. Dispersing layer 3A has a suitable pattern of slits 27 through its surface for dispersing the fluid over the surface of the membrane. Various slit patterns are possible so long as the slits disperse the fluid relatively evenly over that portion of the membrane exposed by opening 30 in the membrane holding layer.

The housings of the invention can be formed of any suitable material. Potentially suitable materials include glass, metals such as stainless steel or aluminum, and plastics. Machinable or moldable plastics will be particularly suitable as housing materials. An injection moldable plastic such as a polycarbonate resin will allow for simple and easy fabrication of the housings. Such a device may be made sufficiently inexpensive so as to be disposable after a single use.

The dispersing layer and membrane holding layer can be made of any suitable material that is formable into a thin film and through which the desired slits and openings may be formed. Films of polycarbonate and polyethylene are used as membranes for culturing cells and should prove suitable for use in the present invention. A polyester film, e.g. Dupont Mylar™, may also prove suitable.

FIG. 2 depicts device 10 as it appears when assembled. As can be seen therein, the assembled device is compact and of simple construction. Additionally, the internal volume of the device is quite small. This is advantageous in that only small amounts of fluid are required for circulation through the device. It is contemplated that the housings of the device may be made about two inches square and less than one-half inch in height. The fluid volume between the interior of the housing and the membrane may be on the order of a few hundred microliters.

The various parts of the device may be held together by a suitable adhesive between them around the periphery of the device. Alternatively, the housings could be clamped together or held together by plastic welds. The housings could also be provided with a suitable snap-together fastening means so that the two halves of the device could be assembled and disassembled quickly and simply. In cases in which a sheet of tissue is to be used as a membrane, one of the housings may be provided with a set of pins around its periphery. These pins will pierce the membrane and mate with a corresponding set of holes in the other housing. These pins and holes will be generally similar to those depicted in Sweetana et al, U.S. Pat. No. 5,183,760, previously incorporated herein by reference.

The embodiment depicted in FIG. 1 is a two-sided device including two symmetric halves above and below the membrane. Such a device will be particularly useful for studying the transport of drugs or other substances across the membrane. For example, a permeable membrane may be provided with a layer of tissue supported thereon. Fluid carrying a substance of interest may be circulated through one of the housings. By sampling fluid circulating through the other housing on the other side of the membrane, and determining the concentration of the substance that appears in that fluid, the transport characteristics of the substance across the membrane may be calculated or inferred.

Figure 5:
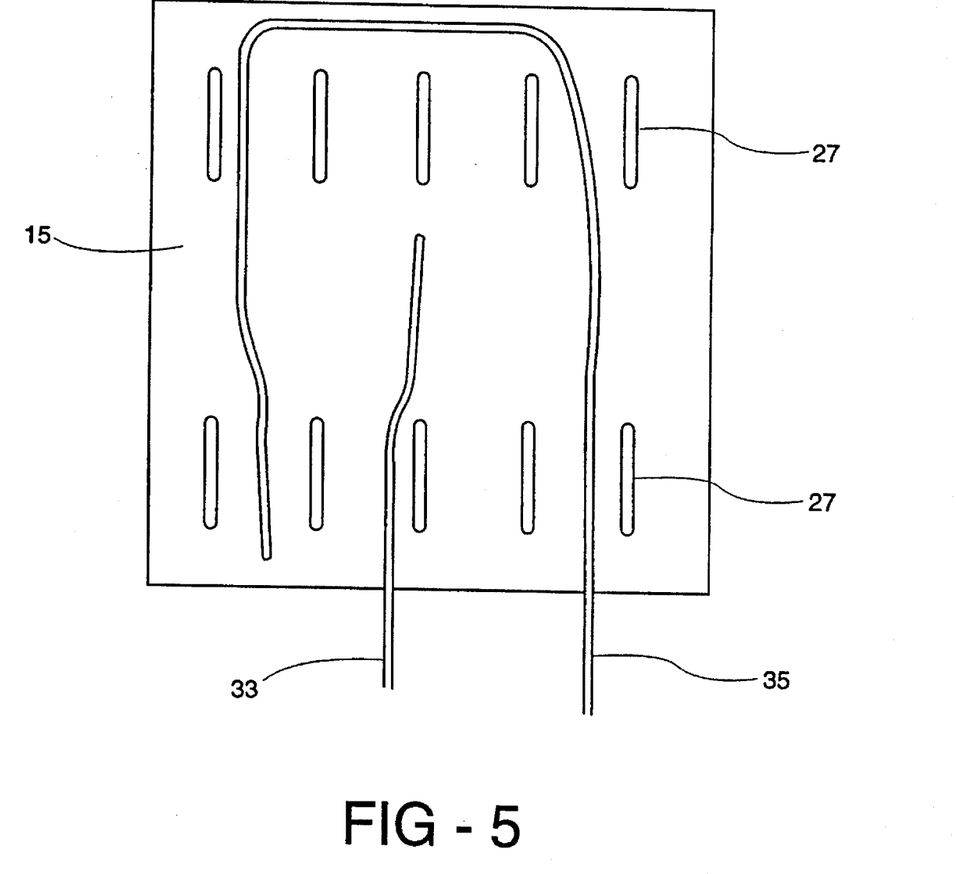
FIG. 5 shows voltage sensing and current electrodes disposed over a dispersing layer for use in the device of FIG. 1.

In some cases, one or more electrodes may be provided, preferably on the surface of dispersing layer 15 as depicted in FIG. 5. These electrodes, which may be in the form of thin wires or conductive foil strips, are sandwiched between the dispersing layer and one side of the membrane. A voltage sensing electrode 33 is depicted at the center of the dispersing layer. The voltage across the membrane can be determined by measuring the potential difference between two voltage sensing electrodes, one on each side of the membrane.

A current electrode 35 is also depicted in FIG. 5. A voltage difference, generally resulting in the flow of current across the membrane, may be applied by applying a differential voltage between two current electrodes, one on each side of the membrane. As depicted in FIG. 5, current electrode 35 will advantageously be in the form of a loop around the dispersing layer so that a relatively evenly dispersed current may be induced across a large portion of the exposed membrane.

In some cases, a non-porous film may be used as a membrane. This provides two separate chambers, one on each side of the membrane, for performing experiments or culturing cells. If desired, a single sided device may be used in which the membrane is exposed by omitting one of the housings. This provides access to one side of the membrane so that it may be viewed with a microscope, for example. In addition, the film can be constructed so that it can be easily peeled away to expose the cells for direct manipulation or examination.

The fluid circulated through the device on either side of the membrane may be liquid or gas. Circulation of gases over the membranes may be useful, for example, to study the delivery of drugs by aerosols, or to study the toxic effects of airborne materials. The fluid circulated over the membrane may usually be an aqueous solution of a particular substance of interest, e.g., a given drug or toxin. In some cases the fluid may be a nutrient bath for culturing cells on the surface of the membrane.

Figure 6:
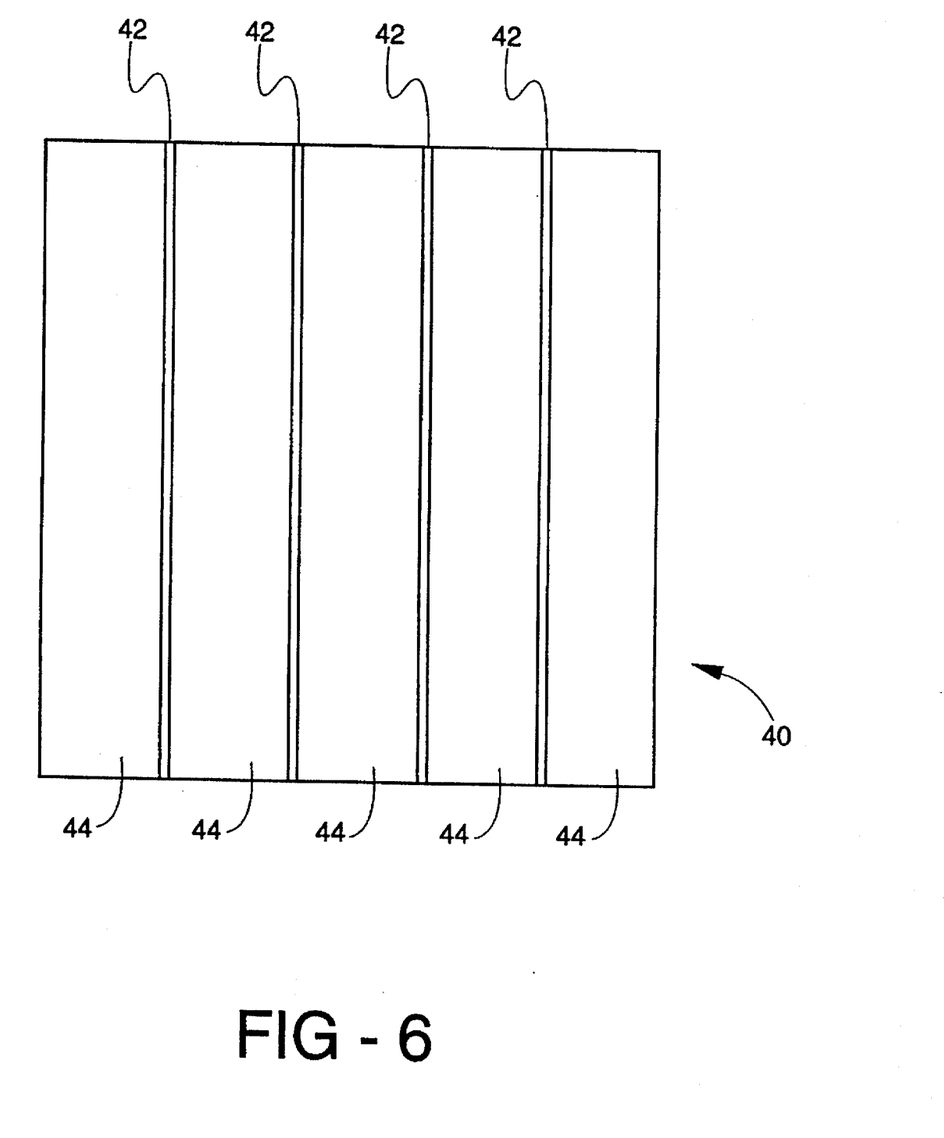
FIG. 6 depicts a special ridged membrane for some uses in the device of FIG. 1.

FIG. 6 depicts a ridged membrane 40, which may sometimes be used in place of the flat membrane 20 shown in FIG. 1. Ridged membrane 40 includes a series of ridges 42 running parallel to the fluid flow path, i.e., parallel to the slits in dispersing layer 15. Ridges 42 define a series of parallel channels 44 on the surface of the membrane.

Different types of cells may be grown in each of the channels defined by the ridges. When a fluid is circulated over the membrane, the effect of that fluid on each different type of cells may be conveniently studied and compared. For example, the ridged membrane depicted in FIG. 6 provides five discrete channels in which five different kinds of cells may be exposed to the same fluid in a single device.

Generally, the ridges should be of sufficient height to contact and form something of a seal against the dispersing layer. This will prevent cells in a given channel from overgrowing the ridge into an adjacent channel.

Figure 7:
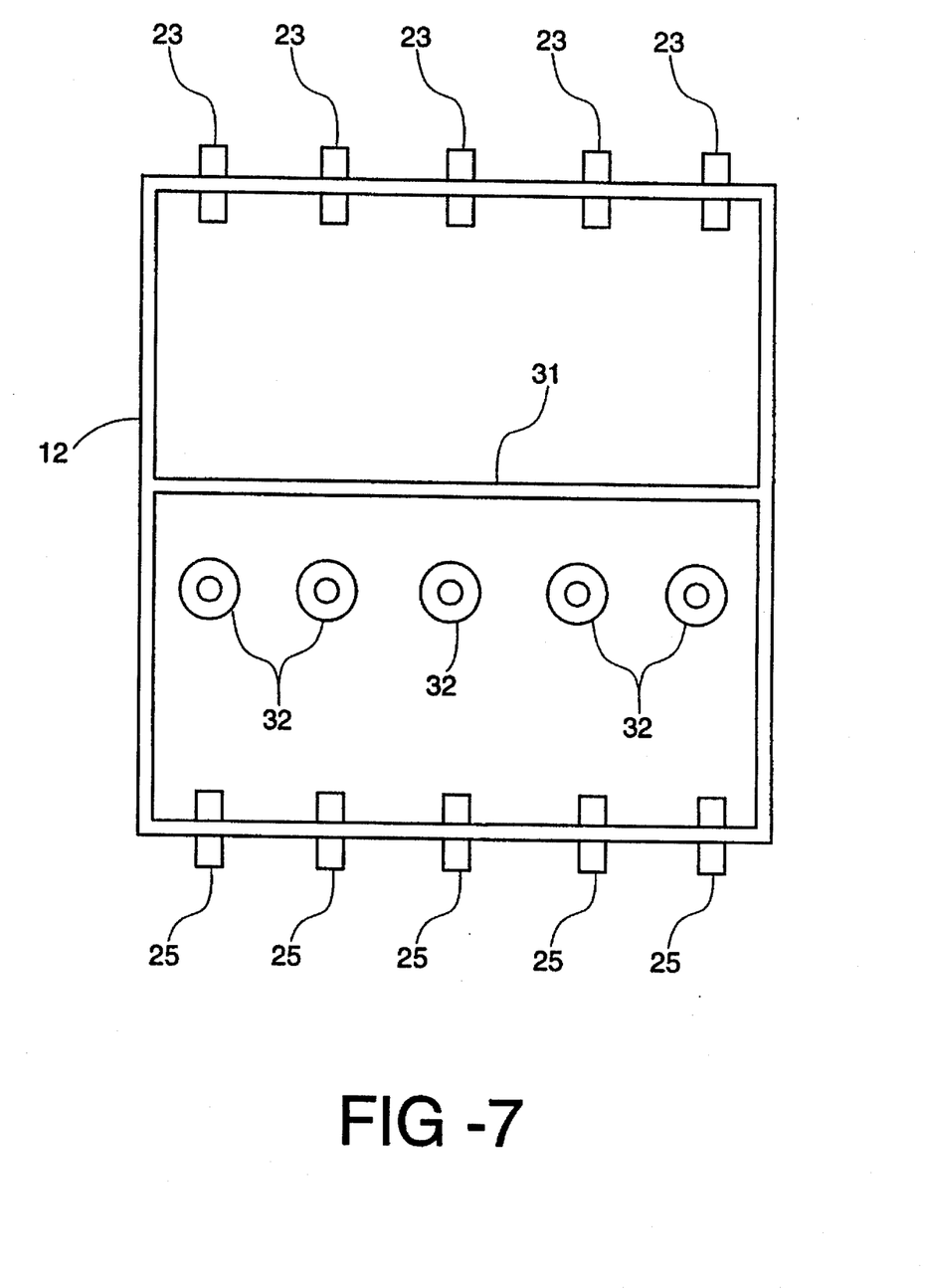
FIG. 7 depicts an alternate housing having a plurality of fluid inlets, outlets, and injection ports.

FIG. 7 depicts a further embodiment of the housing particularly adapted for use with a ridged membrane. In this embodiment, housing 12 is provided with a plurality of inlets 23 and outlets 25, one inlet and outlet for each channel 44 on ridged membrane 40 (see FIG. 6). Note that in this embodiment, the inlets and outlets are parallel to the fluid flow path across the membrane.

If an adequate seal is formed between the ridges and the dispersing layer, a separate fluid can be flowed along each channel of a single ridged membrane within a single housing. The same or different types of cells may be grown in each channel. Referring again to FIG. 7, the housing depicted has a plurality of injection ports 32. Each injection port corresponds to a single channel of the ridged membrane so that cells may be injected into each channel.

A particular embodiment of the invention has been described in detail for purposes of illustration. Modifications may be made to the embodiment described without departing from the principles of the invention. Therefore, the scope of the invention should be ascertained primarily with reference to the appended claims, along with the full scope of equivalents to which those claims are entitled.

What is claimed is:

1. A device for circulating fluid over a membrane, the device comprising:

a housing that in combination with the membrane defines an enclosed volume;

means for circulating fluid through the enclosed volume defined by the housing and the membrane, said circulating means comprising an inlet and an outlet in the housing, said inlet disposed to allow fluid to enter the enclosed volume in a direction generally parallel to the membrane;

a dispersing member disposed in the enclosed volume and laterally spaced-apart from said membrane, said dispersing member defining at least a first and a second opening spaced over an exposed surface of the membrane, wherein the inlet and the outlet are disposed between the housing and the dispersing member; and a divider between the inlet and the outlet for directing the fluid entering through the inlet to flow through the first opening in the dispersing member in the direction of the membrane, across the membrane, through the second opening in the dispersing member and out the outlet.

2. The device of claim 1, further comprising:

a membrane holding layer disposed between the membrane and the dispersing member, said holding layer defining an opening that exposes the surface area of the membrane to the enclosed volume.

3. The device of claim 1 further comprising:

an electrode within the enclosed volume.

4. The device of claim 1, further comprising:

at least one electrode formed on the surface of the dispersing member nearest the membrane.

5. The device of claim 1, wherein the membrane has at least one ridge defining at least two parallel channels within the enclosed volume.

6. A device for circulating fluid over two sides of a membrane, the device comprising:

a first housing that in combination with a first side of the membrane defines a first enclosed volume;

means for circulating fluid through the first enclosed volume, said circulating means comprising an inlet and an outlet in the first housing, said inlet disposed to allow fluid to enter the enclosed volume in a direction generally parallel to the membrane;

a dispersing layer disposed in the first enclosed volume and laterally spaced-apart from the first side of said membrane, said dispersing layer defining at least a first and a second opening spaced over an exposed surface on the first side of the membrane, wherein the inlet and the outlet are disposed between the housing and the dispersing layer;

a divider between the inlet and the outlet for directing the fluid entering through the inlet to flow through the first opening in the dispersing layer in the direction of the first side of the membrane, across the first side of the membrane, through the second opening in the dispersing member and out the outlet;

a second housing that in combination with a second side of the membrane defines a second enclosed volume; and means for circulating fluid through the second enclosed volume.

7. The device of claim 6, wherein the means for circulating fluid through the second enclosed volume comprises an inlet and an outlet in fluid communication with the second enclosed volume.

8. The device of claim 6, further comprising:

a membrane holding layer disposed between the first side of the membrane and the dispersing layer, said membrane holding layer defining an opening that exposes the surface area of the membrane to the first enclosed volume.

9. The device of claim 8, further comprising:

a second membrane holding layer disposed adjacent the second side of the membrane, said second membrane holding layer defining an opening that exposes a predetermined surface area of the membrane to the second enclosed volume.

10. The device of claim 6, further comprising:

a second dispersing layer disposed in the second enclosed volume and laterally spaced-apart from the second side of the membrane, said second dispersing layer defining a plurality of openings spaced over a second surface of the membrane, and wherein the means for circulating fluid through the second enclosed volume comprises a second inlet and a second outlet; and a second divider between the second inlet and the second outlet, wherein the second inlet and the second outlet are disposed between the second housing and the second dispersing layer, whereby fluid enters into the second enclosed volume through the second inlet, passes through one of the openings in the second dispersing layer, is dispersed over the second surface of the membrane, passes through another of the openings in the second dispersing layer, and exists through the second outlet.

11. The device of claim 10, further comprising:

a pair of electrodes, an electrode disposed between each of the first and second dispersing layers and the membrane.

12. The device of claim 11, wherein the electrodes are formed on the surfaces of the dispersing layers nearest the membrane.

13. The device of claim 10, further comprising a second membrane holding layer disposed between the second side of the membrane and the second dispersing layer.

14. The device of claim 10, further comprising:

an electrode on each of the first and second dispersing layers on the side nearest the membrane.

15. The device of claim 6, further comprising:

an electrode disposed inside at least one of the two enclosed volumes.

16. The device of claim 15, wherein an electrode is disposed inside each of the two enclosed volumes.

17. The device of claim 6, wherein the membrane has at least one ridge defining at least two parallel channels within one of the first and second enclosed volumes.

18. A method for circulating a fluid over a membrane, the method comprising:

circulating the fluid through a housing that in combination with the membrane defines an enclosed volume, wherein the circulating step further comprises introducing the fluid into the enclosed volume through an inlet in a direction that is generally parallel with the membrane, directing the fluid with a first side of a divider to pass through at least one opening in a dispersing member that is laterally spaced-apart from the membrane so that the fluid is directed generally toward the membrane as it passes through the dispersing member, passing the fluid along the membrane, and directing the fluid back through another opening in the dispersing member so that the fluid may exit the housing through an outlet on a second side of the divider.

19. The method of claim 18, further comprising:

passing the fluid through an opening in a membrane holding layer disposed between the membrane and the dispersing member, said holding layer defining an opening that exposes a predetermined surface area of the membrane to the enclosed volume.

20. The method of claim 18, wherein the membrane has at least one ridge defining at least two parallel channels within the enclosed volume.

21. A method for circulating fluids over two sides of a membrane, the method comprising:

circulating a first fluid through a first housing that in combination with a first side of the membrane defines a first enclosed volume, wherein the step of circulating the first fluid further comprises introducing the first fluid into the first enclosed volume through a first inlet in a direction that is generally parallel with the first side of the membrane, directing the first fluid with the first side of a divider to pass through at least one opening in a dispersing layer that is laterally spaced-apart from the first side of the membrane so that the first fluid is directed generally toward the first side of the membrane as it passes through the dispersing layer, passing the first fluid along the first side of the membrane, and directing the fluid back through another opening in the dispersing member so that the fluid may exit the housing through an outlet on a second side of the divider; and circulating a second fluid through a second housing that in combination with a second side of the membrane defines a second enclosed volume.

22. The method of claim 21, further comprising:

measuring a potential difference across the membrane by measuring a potential difference between two electrodes, one electrode on each side of the membrane.

23. The method of claim 21, further comprising:

applying a potential difference across the membrane by applying a potential difference between two electrodes, one electrode on each side of the membrane.

24. The method of claim 21, wherein a substance of interest is carried by the first fluid and further comprising the step of detecting the presence of the substance of interest in the second fluid.

* * * * *